United States Patent
Claude et al.

(10) Patent No.: US 7,361,368 B2
(45) Date of Patent: Apr. 22, 2008

(54) DEVICE AND METHOD FOR COMBINING A TREATMENT AGENT AND A GEL

(75) Inventors: Charles D. Claude, San Jose, CA (US); Paul J. Kawula, Sunnyvale, CA (US); Syed Faiyaz Ahmed Hossainy, Fremont, CA (US); Kimchi Tran, Milpitas, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 562 days.

(21) Appl. No.: 10/187,007

(22) Filed: Jun. 28, 2002

(65) Prior Publication Data

US 2004/0002692 A1 Jan. 1, 2004

(51) Int. Cl.
*A61F 2/00* (2006.01)
*A61K 9/22* (2006.01)

(52) U.S. Cl. .................... 424/426; 604/891.1

(58) Field of Classification Search ............ 424/422, 424/426, 428, 450, 484, 490; 604/890.1, 604/891.1, 101.01, 101.03, 101.05; 623/11.11, 623/23.59; 427/1.42, 2.24, 2.31
See application file for complete search history.

(56) References Cited

U.S. PATENT DOCUMENTS

| | | | |
|---|---|---|---|
| 3,780,733 A | 12/1973 | Martinez-Mangor | |
| 4,617,186 A * | 10/1986 | Schafer et al. ........... | 424/78.04 |
| 4,794,931 A | 1/1989 | Yock | |
| 5,000,185 A | 3/1991 | Yock | |
| 5,024,234 A | 6/1991 | Leary et al. | |
| 5,049,130 A | 9/1991 | Powell | |
| 5,092,848 A | 3/1992 | DeCiutiis | |
| 5,171,217 A | 12/1992 | March et al. | |
| 5,202,745 A | 4/1993 | Sorin et al. | |
| 5,203,338 A | 4/1993 | Jang | |

(Continued)

FOREIGN PATENT DOCUMENTS

EP 0861632 A1 9/1998

(Continued)

OTHER PUBLICATIONS

Wilensky R., et al., "Direct intraarterial wall injection of microparticles via a catheter: a potential drug delivery strategy following angioplasty," American Heart Journal, 122:1136, 1991.*

(Continued)

*Primary Examiner*—Sharon Kennedy
(74) *Attorney, Agent, or Firm*—Blakely, Sokoloff, Taylor & Zafman LLP

(57) ABSTRACT

A method including introducing a treatment agent at a treatment site within a mammalian host; and introducing a bioerodable gel material at the treatment site. An apparatus including a first annular member having a first lumen disposed about a length of the first annular member and a first entry port at a proximal end of the first annular member, and a second annular member coupled to the first annular member having a second lumen disposed about a length of the second annular member and a second entry port at a proximal end of the second annular member, wherein the first annular member and the second annular member are positioned to allow a combining of treatment agents introduced through each annular member at the treatment site.

19 Claims, 4 Drawing Sheets

U.S. PATENT DOCUMENTS

| | | | |
|---|---|---|---|
| 5,270,300 A * | 12/1993 | Hunziker | 514/12 |
| 5,291,267 A | 3/1994 | Sorin et al. | |
| 5,306,250 A * | 4/1994 | March et al. | 604/104 |
| 5,321,501 A | 6/1994 | Swanson et al. | |
| 5,336,252 A | 8/1994 | Cohen | |
| 5,354,279 A | 10/1994 | Hofling | |
| 5,365,325 A | 11/1994 | Kumasaka et al. | |
| 5,372,138 A | 12/1994 | Crowley et al. | |
| 5,380,292 A | 1/1995 | Wilson | |
| 5,437,632 A | 8/1995 | Engelson | |
| 5,455,039 A * | 10/1995 | Edelman et al. | 424/422 |
| 5,459,570 A | 10/1995 | Swanson et al. | |
| 5,464,395 A | 11/1995 | Faxon et al. | |
| 5,465,147 A | 11/1995 | Swanson | |
| 5,485,486 A | 1/1996 | Gilhousen et al. | |
| 5,499,630 A | 3/1996 | Hiki et al. | |
| 5,540,912 A * | 7/1996 | Roorda et al. | 424/422 |
| 5,546,948 A | 8/1996 | Hamm et al. | |
| 5,575,815 A * | 11/1996 | Slepian et al. | 600/36 |
| 5,580,856 A | 12/1996 | Prestrelski et al. | |
| 5,588,432 A | 12/1996 | Crowley | |
| 5,621,610 A | 4/1997 | Moore et al. | |
| 5,642,234 A | 6/1997 | Altman et al. | |
| 5,655,548 A | 8/1997 | Nelson et al. | |
| 5,693,029 A | 12/1997 | Leonhardt | |
| 5,722,403 A | 3/1998 | McGee et al. | |
| 5,740,808 A | 4/1998 | Panescu et al. | |
| 5,785,689 A | 7/1998 | De Toledo et al. | |
| 5,827,313 A | 10/1998 | Ream | |
| 5,843,156 A | 12/1998 | Slepian et al. | |
| 5,879,713 A | 3/1999 | Roth et al. | |
| 5,900,433 A | 5/1999 | Igo et al. | |
| 5,919,449 A | 7/1999 | Dinsmore | |
| 5,935,160 A | 8/1999 | Auricchio et al. | |
| 5,939,323 A | 8/1999 | Valentini et al. | |
| 5,941,868 A | 8/1999 | Kaplan et al. | |
| 5,957,941 A | 9/1999 | Ream | |
| 5,968,064 A | 10/1999 | Selmon et al. | |
| 5,979,449 A | 11/1999 | Steer | |
| 5,981,568 A | 11/1999 | Kunz et al. | |
| 5,997,536 A | 12/1999 | Osswald et al. | |
| 6,022,540 A | 2/2000 | Bruder et al. | |
| 6,045,565 A | 4/2000 | Ellis et al. | |
| 6,051,071 A | 4/2000 | Charvet et al. | |
| 6,056,744 A | 5/2000 | Edwards | |
| 6,058,329 A | 5/2000 | Salo et al. | |
| 6,071,305 A | 6/2000 | Brown et al. | |
| 6,086,582 A | 7/2000 | Altman et al. | |
| 6,093,177 A | 7/2000 | Javier, Jr. et al. | |
| 6,099,563 A | 8/2000 | Zhong | |
| 6,099,864 A | 8/2000 | Morrison et al. | |
| 6,102,887 A | 8/2000 | Altman | |
| 6,102,904 A | 8/2000 | Vigil et al. | |
| 6,102,926 A | 8/2000 | Tartaglia et al. | |
| 6,120,520 A | 9/2000 | Saadat et al. | |
| 6,120,904 A | 9/2000 | Hostettler et al. | |
| 6,133,231 A | 10/2000 | Ferrara et al. | |
| 6,134,003 A | 10/2000 | Tearney et al. | |
| 6,151,525 A | 11/2000 | Soykan et al. | |
| 6,152,141 A | 11/2000 | Stevens et al. | |
| 6,153,428 A | 11/2000 | Gustafsson et al. | |
| 6,159,443 A | 12/2000 | Hallahan | |
| 6,175,669 B1 | 1/2001 | Colston et al. | |
| 6,177,407 B1 | 1/2001 | Rodgers et al. | |
| 6,179,809 B1 | 1/2001 | Khairkhahan et al. | |
| 6,183,432 B1 | 2/2001 | Milo | |
| 6,183,444 B1 | 2/2001 | Glines et al. | |
| 6,187,330 B1 | 2/2001 | Wang et al. | |
| 6,190,353 B1 | 2/2001 | Makower et al. | |
| 6,191,144 B1 | 2/2001 | Isner | |
| 6,193,763 B1 | 2/2001 | Mackin | |
| 6,197,324 B1 | 3/2001 | Crittenden | |
| 6,201,608 B1 | 3/2001 | Mandella et al. | |
| 6,206,893 B1 | 3/2001 | Klein et al. | |
| 6,206,914 B1 | 3/2001 | Soykan et al. | |
| 6,207,180 B1 | 3/2001 | Ottoboni et al. | |
| 6,210,392 B1 | 4/2001 | Vigil et al. | |
| 6,217,527 B1 | 4/2001 | Selmon et al. | |
| 6,217,554 B1 | 4/2001 | Green | |
| 6,221,049 B1 | 4/2001 | Selmon et al. | |
| 6,231,546 B1 | 5/2001 | Milo et al. | |
| 6,235,000 B1 | 5/2001 | Milo et al. | |
| 6,241,710 B1 | 6/2001 | VanTassel et al. | |
| 6,251,104 B1 | 6/2001 | Kesten et al. | |
| 6,283,947 B1 | 9/2001 | Mirzaee | |
| 6,287,285 B1 | 9/2001 | Michal et al. | |
| 6,290,729 B1 | 9/2001 | Slepian et al. | |
| 6,296,602 B1 | 10/2001 | Headley | |
| 6,299,604 B1 | 10/2001 | Ragheb et al. | |
| 6,309,370 B1 | 10/2001 | Haim et al. | |
| 6,315,994 B2 | 11/2001 | Usala et al. | |
| RE37,463 E | 12/2001 | Altman | |
| 6,334,872 B1 | 1/2002 | Termin et al. | |
| 6,346,098 B1 | 2/2002 | Yock et al. | |
| 6,346,099 B1 | 2/2002 | Altman | |
| 6,346,515 B1 | 2/2002 | Pitaru et al. | |
| 6,358,247 B1 | 3/2002 | Altman et al. | |
| 6,358,258 B1 | 3/2002 | Arcia et al. | |
| 6,368,285 B1 | 4/2002 | Osadchy et al. | |
| 6,371,935 B1 | 4/2002 | Macoviak et al. | |
| 6,371,992 B1 | 4/2002 | Tanagho et al. | |
| 6,379,379 B1 | 4/2002 | Wang | |
| 6,385,476 B1 | 5/2002 | Osadchy et al. | |
| 6,391,052 B2 | 5/2002 | Buirge et al. | |
| 6,395,023 B1 | 5/2002 | Summers | |
| 6,409,716 B1 | 6/2002 | Sahatjian et al. | |
| 6,416,510 B1 | 7/2002 | Altman et al. | |
| 6,432,119 B1 | 8/2002 | Saadat | |
| 6,436,135 B1 | 8/2002 | Goldfarb | |
| 6,443,941 B1 | 9/2002 | Slepian et al. | |
| 6,443,949 B2 | 9/2002 | Altman | |
| 6,447,504 B1 | 9/2002 | Ben-Haim et al. | |
| 6,458,098 B1 * | 10/2002 | Kanesaka | 604/101.05 |
| 6,464,862 B2 | 10/2002 | Bennett | |
| 6,478,776 B1 | 11/2002 | Rosenman et al. | |
| 6,482,231 B1 | 11/2002 | Abatangelo et al. | |
| 6,485,481 B1 | 11/2002 | Pfeiffer | |
| 6,494,862 B1 | 12/2002 | Ray et al. | |
| 6,548,081 B2 | 4/2003 | Sadozai et al. | |
| 6,554,801 B1 | 4/2003 | Steward et al. | |
| 6,599,267 B1 | 7/2003 | Ray et al. | |
| 6,628,988 B2 | 9/2003 | Kramer et al. | |
| 6,629,947 B1 | 10/2003 | Sahatjian et al. | |
| 6,632,457 B1 | 10/2003 | Sawhney | |
| 6,635,267 B1 | 10/2003 | Miyoshi et al. | |
| 6,660,034 B1 | 12/2003 | Mandrusov et al. | |
| 6,682,730 B2 | 1/2004 | Mickle et al. | |
| 6,689,608 B1 | 2/2004 | Mikos et al. | |
| 6,692,466 B1 | 2/2004 | Chow et al. | |
| 6,702,744 B2 | 3/2004 | Mandrusov et al. | |
| 6,706,034 B1 * | 3/2004 | Bhat | 604/890.1 |
| 6,737,072 B1 | 5/2004 | Angele et al. | |
| 6,748,258 B1 | 6/2004 | Mueller et al. | |
| 6,749,617 B1 | 6/2004 | Palasis et al. | |
| 6,777,231 B1 | 8/2004 | Katz et al. | |
| 6,790,455 B2 | 9/2004 | Chu et al. | |
| 6,858,229 B1 | 2/2005 | Hubbell et al. | |
| 2001/0023349 A1 | 9/2001 | Van Tassel et al. | |
| 2002/0072706 A1 * | 6/2002 | Hiblar et al. | 604/101.01 |
| 2002/0124855 A1 | 9/2002 | Chachques | |
| 2002/0146557 A1 | 10/2002 | Claude et al. | |
| 2002/0188170 A1 | 12/2002 | Santamore et al. | |
| 2003/0040712 A1 | 2/2003 | Ray et al. | |
| 2003/0078671 A1 | 4/2003 | Lesniak et al. | |

| | | | |
|---|---|---|---|
| 2003/0105493 | A1 | 6/2003 | Salo |
| 2004/0015048 | A1 | 1/2004 | Chiu |
| 2004/0181206 | A1 | 9/2004 | Chiu |
| 2004/0208845 | A1 | 10/2004 | Michal et al. |
| 2004/0213756 | A1 | 10/2004 | Michal et al. |
| 2005/0031874 | A1 | 2/2005 | Michal et al. |
| 2005/0070844 | A1 | 3/2005 | Chow |

FOREIGN PATENT DOCUMENTS

| | | |
|---|---|---|
| EP | 0938871 A2 | 9/1999 |
| GB | 2194144 | 3/1988 |
| WO | WO 92/10142 A1 | 6/1992 |
| WO | WO 98/54301 | 12/1998 |
| WO | WO 00/71196 A1 | 11/2000 |
| WO | WO 0124775 | 4/2001 |
| WO | WO 01/45548 A2 | 6/2001 |
| WO | WO 01/49357 A2 | 7/2001 |
| WO | WO 02/28450 A2 | 4/2002 |
| WO | WO 02/40070 A2 | 5/2002 |
| WO | WO 02/087623 | 11/2002 |
| WO | WO 03/027234 A2 | 4/2003 |
| WO | WO 03/064637 A1 | 8/2003 |
| WO | WO 2004/050013 A2 | 6/2004 |
| WO | WO 2004/066829 A2 | 8/2004 |
| WO | WO 2004/091592 A2 | 10/2004 |

OTHER PUBLICATIONS

Wasielewski, S., "Ischamische Erkrankungen, Gefassneubildung anregen" Deutsche Apotheker Zeitung, vol. 140, No. 3, Jan. 2000, pp. 232-233.

Yamomoto, N. et al., "Histologic Evidence that Basic Fibroblast Growth Factor Enhances the Angiogenic Effects of Transmyocardial Laser Revascularization," Basic Research in Cardiology, vol. 95, No. 1, Feb. 2000, pp. 55-63.

Agocha A. et al. "Hypoxia regulates basal and induced DNA synthesis and collagen type I production in human cardiac fibroblasts: effects of transforming growth factor-beta 1, thyroid hormone, angiotensin II and basic fibroblast growth factor," *J. Mol. Cell. Cardiol.* 29(8): 2233-2244. (Apr. 1997).

Allemann, E. et al. "Kinetics of Blood Component Adsorption on poly(D,L-lactic acid) Nanoparticles: Evidence of Complement C3 Component Involvement," *J. Biomed. Mater Res.* 37(2):229-234 (Nov. 1997), Abstract downloaded from the Internet at: http://www.ncbi.nlm.nih.gov/entrez/query.fcgi?cmd=Retrieve&db=PubMed, 1 page.

Anderson, J. et al. "Biodegradation and Biocompatibility of PLA and PLGA Microspheres," *Advanced Drug Delivery Reviews* 28 (1997), pp. 5-24.

Assmus, B. et al. "Transplantation of Progenitor Cells and Regeneration Enhancement in Acute Myocardial Infarction (TOPCARE-AMI)," *Circulation* (2002), 106:3009-3017, first page only (1 page).

Baxter, "FloSeal Matrix Hemostatic Sealant," downloaded from the Internet on Nov. 14, 2002, from: http://www.fusionmed.com/docs/surgeon/default.asp, 2 pages.

Berger et al. "Poly-L-cysteine," *J. Am. Chem. Soc.* 78(17):4483-4488 (Sep. 5, 1956).

Bernatowicz, M. et al. "Preparation of Boc-[S-(3-nitro-2-pyridinesulfenyl)]-cysteine and its use for Unsymmetrical Disulfide Bond Formation," *Int. J. Peptide Protein Res.* 28(2):107-112 (Aug. 1996).

Boland, E.D. "Electrospinning Collagen and Elastin: Preliminary Vascular Tissue Engineering," *Frontiers in Bioscience* vol. 9, pp. 1422-1432 (May 1, 2004).

Brust, G. "Polyimides," downloaded from the Internet at: http://www.pslc.ws/macrog/imide.htm, 4 pages (© 2005).

Buschmann, I. et al. "Arteriogenesis Versus Angiogenesis: Two Mechanisms of Vessel Growth," *News Physiol. Sci.* vol. 14 (Jun. 1999), pp. 121-125.

Canderm Pharma, "Technical Dossier: Artecoll," downloaded from the Internet on Oct. 22, 2002 from: http://www.canderm.com/artecoll/tech.html, 3 pages.

Capan, Y. et al. "Preparation and Characterization of Poly(D,L-lactide-co-glycolide) Microspheres for Controlled Release of Human Growth Hormone," *AAPS PharmSciTech.* 2003; 4(2): article 28. Downloaded from the Internet at: http://www.aapspharmscitech.org/view.asp?art=pt040228&pdf=yes (12 pages).

Carpino, L. et al. "Tris(2-aminoethyl)amine as a Substitute for 4-(Aminomethyl)piperidine in the FMOC/Polyamine Approach to Rapid Peptide Synthesis," *J. Org. Chem.* 55(5):1673-1675 (Mar. 1990).

Chandy et al. "The Development of Porous Alginate/Elastin/PEG Composite Matrix for Cardiovascular Engineering," *Journal of Biomaterials Applications*, vol. 17 (Apr. 2003), pp. 287-301.

Corbett, S. et al. "Covalent Cross-linking of Fibronectin to Fibrin is Required for Maximal Cell Adhesion to a Fibronectin-Fibrin Matrix," *The Journal of Biological Chemistry*, 272(40):24999-25005 (Oct. 3, 1997).

Creemers, E. et al. "Matrix Metalloproteinase Inhibition After Myocardial Infarction: A New Approach to Prevent Heart Failure?" *Circ. Res.* vol. 89:201-210 (2001).

Crivello, et al. "Synthesis and Photoinitiated Cationic Polymerization of Monomers with the Silsesquioxane Core," *J Polym Science: Part A: Polymer Chemistry* 35:407-425 (1997).

Davis, M.E. et al., "Injectable Self-Assembling Peptide Nanofibers Create Intramyocardial Microenvironments for Endothelial Cells" *Circulation* 111:442-450 (Feb. 2005).

DeRosa et al. "Biodegradable Microparticles for the Controlled Delivery of Oligonucleotides," *Int. J Pharm*, 242:225-228 (Aug. 21, 2002).

Desai, M. et al. "Polymer bound EDC (P-EDC): A convenient reagent for formation of an amide bond," *Tetrahedron Letters* 34(48):7685-7688 (Nov. 1993), Abstract downloaded from the Internet at: http://www.sciencedirect.com, 1 page.

Dinbergs et al. "Cellular Response to Transforming Growth Factor -$\beta$1 and Basic Fibroblast Growth Factor Depends on Release Kinetics & Extracellular Matrix Interactions," *J. Bio Chem* 271(47):29822-29829 (Nov. 22, 1996).

Edelman, E.R. et al. "Controlled & Modulated Release of Basic Fibroblast Growth Factor," *Biomaterials* vol. 12 (Sep. 1991), pp. 619-626.

Etzion, Sharon et al. "Influence of Embryonic Cardiomyocyte Transplantation on the Progression of Heart Failure in a Rat Model of Extensive Myocardial Infarction," *J. Mol. Cell Cardiol.* 33:1321-1330 (May 2001).

Ferrara, N. "Role of Vascular Endothelial Growth Factor in the Regulation of Angiogenesis," *Kidney International* 56(3):794-814 (1999), Abstract downloaded from the Internet at: http://www.nature.com/ki/journal/v56/n3/abs/4490967a.html, 1 page.

Fuchs, S. et al. "Catheter-Based Autologous Bone Marrow Myocardial Injection in No-Option Patients with Advanced Coronary Artery Disease," *J. Am. Coll. Cardiol.* 41(10):1721-1724 (2003).

Fukumoto, S. et al. "Protein Kinase C $\delta$ Inhibits the Proliferation of Vascular Smooth Muscle Muscle Cells by Suppressing $G_1$ Cyclin Expression," The Journal of Biological Chemistry 272(21):13816-13822 (May 1997).

Giordano, F. et al. "Angiogenesis: The Role of the Microenvironment in Flipping the Switch," *Current Opinion in Genetics and Development* (2001), 11:35-40.

Gossler, et al. "Transgenesis by means of blastocyst-derived embryonic stem cell lines," *Proc. Natl. Acad. Sci. USA*, 83:9065-9069 (Dec. 1986).

Grafe, T.H., "Nanofiber Webs from Electrospinning" Presented at the *Nonwovens in Filtration-Fifth International Conference*, Stuttgart, Germany, Mar. 2003, pp. 1-5.

Gref, R. et al. "Biodegradable Long-Circulating Polymeric Nanospheres," *Science* 263(5153):1600-1603 (Mar. 1994), Abstract downloaded from the Internet at: http://www.sciencemag.org/cgi/content/abstract/263/5153/1600, 1 page.

Grund, F. et al. "Microembolization in Pigs: Effects on Coronary Blood Flow and Myocardial Ischemic Tolerance," *AM J. Physiol.* 227 (Heart Circ. Physiol. 46): H533-H542 (1999).

Gupta et al. "Changes in Passive Mechanical Stiffness of Myocardial Tissue with Aneurysm Formation," *Circulation*, 89(5):2315-2326 (May 1994).

Hashimoto, T. et al. "Development of Alginate Wound Dressings Linked with Hybrid Peptides Derived from Laminin and Elastin," *Biomaterials* 25 (2004), pp. 1407-1414.

Heeschen, C. et al. "Nicotine Stimulates Tumor Angiogenesis," *American College of Cardiology* 37(2) Supplement A, pp. 1A-648A (Feb. 2001), Abstract downloaded from the Internet at: http://24.132.160.238/ciw-01acc/abstract_serach_author.cfm?SearchName=Heeschen, 1 page.

Helisch, A. et al. "Angiogenesis and Arteriogenesis--Not yet for prescription," NEUE DIAGNOSTISCHE UND THERAP. VERFAHREN, *Z. Kardiol.* 89:239-244 Steinkopff Verlag (2000).

Hendel, R.C. et al. "Effect of Intracoronary Recombinant Human Vascular Endothelial Growth Factor on Myocardial Perfusion: Evidence for a Dose-Dependent Effect," *Circulation* 101:118-121 (2000).

Henry, R.R. et al. "Insulin Action and Glucose Metabolism in Nondiabetic Control and NIDDM Subjects. Comparison Using Human Skeletal Muscle Cell Cultures" Diabetes, 44(8):936-946 (1995), Abstract downloaded from the Internet at: http://diabetes.diabetesjournals.org/cgi/content/abstract/44/8/936, 1 page.

Holland, N.B. et al. "Biomimetic Engineering of Non-Adhesive glycocalyx-like Surfaces Using Oligosaccharide Surfactant Polymers," *Nature* 392:799-801 (Apr. 1998), Abstract downloaded from the Internet at: http://www.nature.com, 1 page.

Hovinen, J. et al. "Synthesis of 3'-functionalized oligonucleotides on a single solid support," *Tetrahedron Letters* 34(50):8169-8172 (Dec. 1993), Abstract downloaded from the Internet at: http://www.sciencedirect.com, 1 page.

Huang, K. et al. "Synthesis and Characterization of Self-Assembling Block Copolymers Containing Bioadhesive End Groups," *Biomacromolecules* (2002), 3(2):397-406.

Hutcheson, K. et al. "Comparison of Benefits on Myocardial Performance of Cellular Cardiomyoplasty wit hSkeletal Myoblasts and Fibroblasts," *Cell Transplantation* (2000), 9(3):359-368.

Huynh, T.V. et al. "Constructing and Screening cDNA Libraries in λgt10 and λgt11," Chapter 2, in *DNA Clonong, vol. 1: A Pratical Approach*, ed. by D.M. Glover, pp. 49-78.

Indik, Z.. et al. "Production of Recombinant Human Tropoelastin: Characterization and Demonstration of Immunologic and Chemotactic Activity," *Arch. Biochem. Biophys.* 280(1):80-86 (Jul. 1990), Abstract downloaded from the Internet at: http://www.ncbi.nlm.nih.gov/entrez/query.fcgi?cmd=Retrieve&db=PubMed, 1 page.

Iskandrian, A.S. et al. "Nuclear Cardiac Imaging: Principles and Applications," second edition, F.A. Davis Co., Philadelphia (1996), cover page, title page and TOC (5 pages total).

Isner, J.M. "Vascular Endothelial Growth Factor: Gene Therapy and Therapeutic Angiogenesis" *Am. J. Cardiol.* Nov. 19, 1998; 82(10A):63S-64S.

Ito, W. D. et al. "Monocyte Chemotactic Protein-1 Increases Collateral and Peripheral Conductance After Femoral Artery Occlusion," *Circulation Research*, 80(6):829-837, (Jun. 1997).

Johnson, O.L. et al. "The Stabilization & Encapsulation of Human Growth Hormone into Biodegradable Microspheres," *Pharmaceutical Research*, 14(6):730-735 (1997).

Jonasson, P. et al. "Denatured states of human carbonic anhydrase II: an NMR study of hydrogen/deuterium exchange at tryptophan-indole-$H_n$ sites," *FEBS Letters* 445 (1999), pp. 361-365.

Källtorp, M. et al. "Inflammatory Cell Recruitment, Distribution, and Chemiluminescence Response at IgG Precoated-and Thiol Functionalized Gold Surfaces," *J. Biomed. Mater. Res.*, 47:251-259 (1999).

Kawai, K. et al. "Accelerated Tissue Regeneration Through Incorporation of Basic Fibroblast Growth Factor-Impregnated Gelatin Microspheres into Artificial Dermis," *Biomaterials* 21 (2000), pp. 489-499.

Kawasuji, M. et al. "Therapeutic Angiogenesis with Intramyocardial Administration of Basic Fibroblast Growth Factor," *Ann Thorac Surg* 69:1155-1161 (2000), Abstract downloaded from the Internet at: http://ats.ctsnetjournals.org/cgi/content/abstract/69/4/1155, 2 pages.

Kelley et al. "Restraining Infarct Expansion Preserves Left Ventricular Geometry and Function After Acute Anteroapical Infarction," Circulation (1999), 99:135-142.

Kelly, E.B. "Advances in Mammalian and Stem Cell Clonong," *Genetic Engineering News*, 23(7), Apr. 1, 2003, pp. 17-18 and 68 (3 pages total).

Kim, D. et al. "Glow Discharge Plasma Deposition (GDPD) Technique for the Local Controlled Delivery of Hirudin from Biomaterials," *Pharmaceutical Research* (1998), 15(5):783-786.

Kinart et al. "Electrochemical Studies of 2-hydroxy-3-(3,4-dimethyl-9-oxo-9H-thioxanthen-2-yloxy)N,N,N-trimethyl1-1-propanium chloride," *J. Electroanal. Chem* 294 (1990), pp. 293-297.

Kipshidze, N. et al. "Therapeutic Angiogenesis for Critical Limb Ischemia to Limit or Avoid Amputation," *The Journal of Invasive Cardiology* 11(1):25-28, (Jan. 1999).

Klein, S. et al. "Fibroblast Growth Factors as Angiogenesis Factors: New Insights Into Their Mechanism of Action," in *Regulation of Angiogenesis*, I.D. Goldberg and E.M. Rosen (eds.), 1997; 79:159-192.

Klugherz, B. et al. "Gene Delivery From a DNA Controlled-Release Stent in Porcine Coronary Arteries," *Nature Biotechnology* 18:1181-1184, (Nov. 2000).

Kohilas, K. et al. "Effect of Prosthetic Titanium Wear Debris on Mitogen-Induced Monocyte and Lymphoid Activation," *J. Biomed Mater Res.* 47:95-103, (Apr. 1999).

Kwok, Connie et al. "Design of Infection-Resistant Antibiotic-Releasing Polymers: I. Fabrication and Formulation," *Journal of Controlled Release* 62(1999), pp. 289-299.

Laboratory of Liposome Research. "Liposomes: General Properties," downloaded from the Internet on Feb. 9, 2006 at:http://www.unizh.ch/onkwww/lipos.htm, 5 pages.

Laham, R.J., "Intrapericardial Delivery of Fibroblast Growth Factor-2 Induces Neovascularization in a Porcine Model of Chronic Myocardial Ischemia, " *J. Pharmacol Exper Therap* 292(2):795-802, (2000).

Leibovich, S. J. et al. "Macrophage-Induced Angiogenesis is Mediated by Tumor Necrosis Factor-α," *Nature* 329 (Oct. 15, 1987), pp. 630-633.

Leor, J. et al. "Bioengineered Cardiac Grafts-A New Approach to Repair the Infarcted Myocardium?" *Circulation* (2000); 102[suppl III] III-56-III-61.

Leor, J. et al. Gene Transfer and Cell Transplant: An Experimental Approach to Repair a 'Broken Heart', *Cardiovascular Research* 35 (1997), pp. 431-441.

Leroux, J.C. et al. "An Investigation on the Role of Plasma and Serum Opsonins on the Internalization of Biodegradable poly(D,L-lactic acid) Nanoparticlaes by Human Monocytes," *Life Sci.* 57(7):695-703 (1995), Abstract downloaded from the Internet at: http://www.ncbi.nlm.gov/entrez/query.fcgi?cmd=Retrieve&db=pubmed, 1 page.

Lewin, Benjamin. "Repressor is Controlled by a Small Molecule Inducer", *Genes VII*, Oxford University Press, 7th ed., pp. 227-280, (2000).

Li, J. et al. "PR39, A Peptide Regulator of Angiogenesis," *Nature Medicine* 6(1):49-55, (Jan. 2000).

Li, Ren-Ke et al. "Cell Therapy to Repair Broken Hearts,"*Can. J. Cardiol.* 14(5):735-744 (May 1998).

Li, W.W. et al. "Lessons to be Learned from Clinical Trials of Angiogenesis Modulators in Ischemic Diseases," Chapter 33, in Rubanyi, G. (ed). *Angiogenesis in Health & Disease: Basic Mechanisms and Clinical Applications*, Marcel Dekker, Inc. New York (2000).

Li, Y.Y. et al. "Differential Expression of Tissue Inhibitors of Metalloproteinases in the Failing Human Heart," *Circulation* 98(17):1728-1734, (1998).

Lindsey, M. et al. "Selective Matrix Mettalloproteinase Inhibition Reduces Left Ventricular Remodeling but does not Inhibit Angiogenesis after Myocardial Infarction," *Circulation* 105(6):753-758, (2002).

Long, D.M.et al. "Self-Cleaving Catalytic RNA, " *FASEB Journal*, 7:25-30, (1993).

Lopez, J. J. et al. "Angiogenic Potential of Perivascularly Delivered aFGF in a Porcine Model of Chronic Myocardial Ischemia," *Am. J. Physiol.* 274 (*Heart Circ. Physiol.* 43):H930-H936, (1998).

Lopez, J. J. et al. "VEGF Administration in Chronic Myocardial Ischemia in Pigs," *Cardiovasc Res.* 40(2):272-281 (1998), Abstract downloaded from the Internet at: http://www.ncbi.nlm.nih.gov/entrez/query.fcgi?cmd=Retrieve&db=pubmed, 1 page.

Lu, L. et al. "Biodegradable Polymer Scaffolds for Cartilage Tissue Engineering," in *Clinical Orthopaedics and Related Research*, Carl T. Brighton (ed.). No. 391S, pp. S251-270, (2001).

Luo, Y. et al. "Cross-linked Hyaluronic Acid Hydrogel Films: New Biomaterials for Drug Delivery," *Journal of Controlled Release*, 69:169-184, (2000).

Lyman, M.D. et al. "Characterization of the Formation if Interfacially Photopolymerized Thin Hydrogels in Contact with Arterial Tissue," *Biomaterials*, 17(3):359-64, (1996).

Mansour, S. et al. "Disruption of the proto-oncogene *int-2* in mouse embryo-derived stem cells: a general strategy for targeting mutations to non-selectable genes," *Nature*, 336:348-352, (1988).

Martin, S.L. et al. "Total Synthesis and Expression in *Escherichia Coli* of a Gene Encoding Human Tropoelastin," *Gene* (1995), Abstract, 1 page.

McDevitt, T. et al. "*In vitro* Generation of Differentiated Cardiac Myofibers on Micropatterned Laminin Surfaces," *J. Biomed Mater Res.* 60:472-479, (2002).

Narmoneva, D.A. et al. "Self-assembling short oligopeptides and the promotion of angiogenesis," *Biomaterials* 26 (2005) 4837-4846.

Nguyen, Kytai T. et al. "Photopolymerizable Hydrogels for Tissue Engineering Applications," *Biomaterials* 23:4307-4314, (2002).

Nikolic, S.D. et al. "New Angiogenic Implant Therapy Improves Function of the Ischemic Left Venticle," supplement to *Circulation. Abstracts From Scientific Sessions 2000*, 102(18):II-689, Abstract 3331 (Oct. 2000).

Nitinol Technical Information, "NiTi Smart Sheets, " downloaded from the Internet on Dec. 10, 2002 at: http://www.sma-inc.com/information.html, 1 page.

Ohyanagi, H. et al. "Kinetic Studies of Oxygen and Carbon Dioxide Transport into or from Perfluorochemical Particles," *Proc. ISAO vol. 1 (Artificial Organs vol. 2 (Suppl.))*, pp. 90-92 (1977).

Ozbas, B. et al. "Salt-Triggered Peptide Folding and Consequent Self-Assembly into Hydrogels with Tunable Modulus," *Macromolecules* 37(19):7331-7337, (2004).

Ozbas-Turan, Suna. "Controlled Release of Interleukin-2 from Chitosan Microspheres," *Journal of Pharmaceutical Sciences* 91(5):1245-1251, (May 2002).

Palmiter R. et al. "Germ-Line Transformation of Mice," *Ann. Rev. Genet.* 20:465-499, (1986).

Patrick, C.R. "Mixing and Solution Properties of Organofluorine Compounds," Chapter 10, in Preparation, Properties and Industrial Applications of Organofluorine Compounds, R.E. Banks (ed.), 1st edition, pp. 323-342, Ellis-Horwood Ltd., Chichester:England (1982).

PCT Invitation to Pay Additional Fees for International Appln No. PCT/US03/18360, mailed Nov. 4, 2003 (3 pgs).

PCT International Search Report for International Appln No. PCT/US03/18360, mailed Jan. 28, 2004 (7pgs).

PCT International Search Report for International Appln. No. PCT/US03/30464, mailed Feb. 9, 2004 (5 pages).

PCT International Search Report and Written Opinion for International Appln. No. PCT/US2004/011356, mailed Nov. 24, 2004 (12 pages).

PCT International Preliminary Report on Patentability for International Appln. No. PCT/US2004/011356, mailed Nov. 3, 2005 (6 pgs).

PCT International Search Report and Written Opinion for International Appln No. PCT/US2005/045627, mailed Oct. 13, 2006 (15 pgs).

Peattie, R.A. et al. "Stimulation of In Vivo Angiogenesis by Cytokine-Loaded Hyaluronics Acid Hydrogel Implants," *Biomaterials* (Jun. 2004) 25(14), Abstract downloaded from: www.sciencedirect.com, 2 pages.

Penta, K. et al. "Dell Induces Integrin Signaling and Angiogenesis by Ligation of $\alpha V \beta 3$," *J. Biolog. Chem.* 274(16):11101-11109, (Apr. 1999).

Perin, E.C. et al. "Transendocardial, Autologous Bone Marrow Cell Transplantation for Severe, Chronic, Ischemic Heart Failure," *Circulation* (2003), 1 page.

Pouzet, B. et al. "Is Skeletal Myoblast Transplantation Clinically Relevant in the Era of Angiotensin-Converting Enzyme Inhibitors?" *Circulation* 104[suppl I]:I-223 - I-228, (Sep. 2001).

Prather et al. "Nuclear Transplantation in Early Pig Embryos, " *Biol. Reprod*. 41:414-418, (1989).

ProSci Incorporated, "ILPIP (CT) Peptide," 1 page.

Quellec, P. et al. "Protein Encapsulation Within Polyethylene Glycol-coated Nanospheres. I. Physicochemical Characterization," *J. Biomed. Mater. Res.* 42(1), (1998) Abstract, 1 page.

Ramirez-Solis, R. et al. "Gene Targeting in Embryonic Stem Cells," *Methods in Enzymology*, 225:855-878, (1993).

Rowley, J. et al. "Alginate Hydrogels as Synthetic Extracellular Matrix Materials," *Biomaterials* 20:45-53, (1999).

Sawhney, A.S. et al. "Bioerodible Hydrogels Based on Photopolymerized Poly(ethylene glycol)-co-poly(a-hydroxy acid) Diacrylate Macromers," *Macromolecules* 26(4):581-587, (1993).

Sbaa-Ketata, E. et al. "Hyaluronan-Derived Oligoasaccharides Enhance SDF-1-Dependent Chemotactic Effect on Peripheral Blood Hematopoietic CD $34^+$Cells," *Stem Cells* (2002), 20(6):585-587, "Letter to the Editor" downloaded from the Internet at: http://stemcells.alphamedpress.org/cgi/content/full/20/6/585, 5 pages.

Segura, T. et al. "[216c]-DNA Delivery From Hyaluronic Acid/Collagen Hydrogels," AIchE Technical Program Paper Detail, *American Institute of Chemical Engineers* (ALCHE Annual Meeting 2003), Abstract downloaded from the Internet at: http://www.aiche.org/cofnerences/techprogram/paperdetail.asp?PaperID=1465&DSN=annual, 2 pages.

Segura, T. et al. "Crosslinked Hyaluronic Acid Hydrogels: A Strategy to Functionalize and Pattern," *Biomaterials* 26:359-371, (2005).

Segura, T. et al. "Substrate-Mediated DNA Delivery: Role of the Cationic Polymer Structure and Extent of Modification," *Journal of Controlled Release* 93:69-84, (2003).

Segura, T. et al. "Surface-Tethered DNA Complexes for Enhanced Gene Delivery," *Bioconjugate Chem* 13(3):621-629, (2002).

Shibasaki, F. et al. "Suppression of Signalling Through Transcription Factor NF-AT by Interactions Between Calcineurin and Bcl-2," *Nature* (1997) 386(6626), Abstract downloaded from the Internet at: http://www.ncbi.nlm.nih.gov/entrez/query.fcgi?CMD=Text&DB=pubmed, 1 page.

Shin, H. et al. "Attachment, Profileration, and Migration of Marrow Stromal Osteoblasts Cultured on Biomimetic Hydrogels Modified with an Osteopontin-Derived Peptide," *Biomaterials* 25:895-906, (2004).

Shin, H. et al. "In Vivo Bone & Soft Tissue Response to Injectable, Biodegradable oligo(poly(ethylene glycol) fumerate) Hydrogels," *Biomaterials* 24:3201-3211, (Mar. 2003).

Shu, et al. "Disulfide-crosslinked hyaluronan-gelatin hydrogel films: a covalent mimic of the extracellular matrix for in vitro cell growth," *Biomaterials* (Sep. 2003) 24(21)3825-3834, Abstract downloaded from the Internet at://www.sciencedirect.com, 1 page.

Simons, M. et al. "Clinical Trials in Coronary Angiogenesis: Issues, Problems, Consensus - An Expert Panel Summary," *Circulation* 102:e73-e86, (Sep. 2000), pp. 1-14.

Spenlehauer, G. et al. "In vitro and in vivo Degradation of poly (D,L lactide/glycolide) Type Microspheres Made by Solvent Evaporation Method," *Biomaterials* 10:557-563, (Oct. 1989).

Spinale, Francis G. "Matrix Metalloproteinases - Regulation and Dysregulation in the Failing Heart," *Circ. Res.* 90:520-530, (2002).

Springer, M. et al. "Angiogenesis Monitored by Perfusion with a Space-Filling Microbead Suspension," *Mol. Ther.* (2000) 1(1):82-87, Abstract downloaded from the Internet at: http://www.ncbi.nlm.nih.gov/entrez/query.fcgi?cmd=Retrieve&db=PubMed, 1 page.

Storm, G. et al. "Surface Modification of Nanoparticles to Oppose Uptake by the Mononuclear Phagocyte System," *Advanced Drug Delivery Reviews* (Oct. 1995), 17(1):31-48, Abstract downloaded from the Internet at: http://www.sciencedirect.com, 1 page.

Strauer, B. et al. "Repair of Infarcted Myocardium by Autologous Intracoronary Mononuclear Bone Marrow Cell Transplantation in Humans," *Circulation* 106:1913-1918, (2002).

Tybulewicz, V. et al. "Neonatal lethality and lymphopenia in mice with a homozygous disruption of the c-*abl* proto-oncogene," *Cell* (Jun. 1991), 65(7):1153-1163, Abstract downloaded from the Internet at: http://www.sciencedirect.com, 2 pages.

Unger, E.F. et al. "Effects of a Single Intracoronary Injection of Basic Fibroblast Growth Factor in Stable angina Pectoris" *Am. J. Cardiol* 85(12):1414-1419 (Jun. 2000), Abstract downloaded from the Internet at http://www.sciencedirect.com, 2 pages.

van der Giessen, W.J. et al. "Marked Inflammatory Sequelae to Implantation of Biodegradable and Nonbiodegradable Polymers in Porcine Coronary Arteries," *Circulation* 94(7):1690-1697 (Oct. 1996).

van Luyn, M.J.A. et al. "Cardiac Tissue Engineering: Characteristics of In Unison Contracting Two-and Three-Dimensional Neonatal Rat Ventricle Cell (Co)-Cultures," *Biomaterials* 23:4793-4801, (2002).

Vercruysse, K.P. et al. "Synthesis and in Vitro Degradation of New Polyvalent Hydrazide Cross-Linked Hydrogels of Hyaluronic Acid," *Bioconjugate Chem* 8(5):686-694 (1997), Abstract downloaded from the Internet at: http://pubs.acs.org/cgi-bin/abstract.cgi/bcches/1997/8/i05/abs/bc9701095.html, 1 page.

Visscher, G.E. et al. "Tissue Response to Biodegradable Injectable Microcapsules," *Journal of Biomaterials Applications* 2 (Jul. 1987), pp. 118-119.

Vlodavsky, I. et al. "Extracellular Matrix-resident Basic Fibroblast Growth Factor: Implication for the Control of Angiogenesis,"*J. Cell Biochem*, 45(2):167-176 (Feb. 1991), Abstract downloaded from the Internet at: http://www.ncbi.nlm.nih.gov/entrez/query.fcgi?cmd=Retrieve&db=PubMed, 1 page.

Witzenbichler, B., et al. "Vascular Endothelial Growth Factor-C (VEGF-C/VEGF-2) Promotes Angiogenesis in the Setting of Tissue Ischemia" *AM Pathol*. 153(2):381-394, (Aug. 1998).

Zervas, L. et al. "On Cysteine and Cystine Peptides. II. S-Acylcysteines in Peptide Synthesis," *J. Am. Chem. Soc.* 85(9):1337-1341, (May 1963).

Zheng, W. et al. "Mechanisms of coronary angiogenesis in response to stretch: role of VEGF and TGF-beta," *Am J Heart Circ Physiol*. 280(2):H909-H917, (Feb. 2001).

Zimmermann, W. et al. "Engineered Heart Tissue for Regeneration of Diseased Hearts," Biomaterials 25:1639-1647, (2004).

\* cited by examiner

DEVICE AND METHOD FOR COMBINING A TREATMENT AGENT AND A GEL

BACKGROUND

1. Field

The invention relates to retaining a treatment agent at a treatment site with a bioerodable gel.

2. Relevant Art

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a method and apparatus for delivering agents to help stimulate the natural process of therapeutic angiogenesis to compensate for blood loss due to an occlusion in a coronary and peripheral arteries in order to treat ischemia.

In some therapies, e.g., cardiovascular-related, cancer-related, and certain surgical or minimally-invasive therapies, it may be desirable to inject a treatment agent of or including a sustained release matrix intralumenally, intracardially, or intraventricularly. Unfortunately, however, it is generally difficult to retain the treatment agent at a desired treatment site. In cardiovascular-related therapies, for example, rarely is greater than 30 percent of the sustained release matrix retained at the injection site following such therapies. The loss of sustained release matrix generally occurs either during the initial injection or as a result of backflow from the needle site. The backflow from the needle site can occur due to an excessive amount of fluid required to deliver the matrix material, or, as the needle is removed from the injection site, the site does not seal before matrix material escapes. The consequences of matrix material escaping can be multifold depending on the interaction of the matrix and the surrounding blood or fluid.

The loss of matrix material and release can result in inconsistent dosage delivery. The inconsistency in dosage delivery in turn results in the delivery of the treatment agent that possibly will be at a dosage outside of the desired or optimum therapeutic window. In the case of arterial or ventricular treatment sites, a second response would occur if the sustained release matrix has thrombogenic effects, resulting in the formation of thrombosis that may have severe consequences in the arterial or ventricular region.

What is needed is a technique for retaining a treatment agent, including a treatment agent of or including a sustained-release matrix at a treatment site.

SUMMARY

A method is disclosed. In one embodiment, the method includes introducing a treatment agent at a treatment site within a mammalian host and introducing a bioerodable gel at the treatment site. Representatively, the gel includes a substance that will retain the treatment agent at a desired treatment site. In one example, the treatment agent and gel may be introduced as a combination. Alternatively, the treatment agent and gel may be introduced sequentially, such as introducing the gel before and/or after the treatment agent. The gel may serve, in one aspect, to retain the treatment agent at the treatment site for a prolonged period of time so as to beneficially stimulate the effect of a treatment agent. Suitable treatment sites representatively include, but are not limited to, in or around a blood vessel such as a coronary blood vessel, thoroscopic surgery sites, orthoscopic surgery sites, and laparoscopic surgery sites.

In another embodiment, a method includes introducing a delivery device at a location in a blood vessel and advancing the delivery device a distance into a wall (including entirely through the wall) of the blood vessel to a treatment site. After the introduction of the delivery device, the method contemplates introducing an agent and a gel, such as a bioerodable gel, at the treatment site. Again, the treatment agent and the bioerodable gel may be introduced simultaneously or sequentially as described above.

In yet another embodiment, a kit (e.g., a pre-manufactured package) is disclosed. A suitable kit includes a treatment agent and a compound having a property that forms a bioerodable gel within a mammalian host. The kit may be suitable, in one example, in the methods described above.

In a further embodiment, an apparatus is disclosed. In one embodiment, the apparatus includes a first annular member having a first lumen disposed about a length of the first annular member, and a second annular member coupled to the first annular member having a second lumen disposed about a length of the second annular member, wherein collectively the first annular member and the second annular member have a diameter suitable for placement at a treatment site within a mammalian body. Representatively, distal ends of the first annular member and the second annular member are positioned with respect to one another to allow a combining of treatment agents introduced through each of the first annular member and the second annular member to allow a combining of treatment agents at the treatment site. Such an apparatus is particularly suitable for delivering a multi-component gel material (i.e., individual components through respective annular members) that forms a bioerodable gel within a mammalian host.

BRIEF DESCRIPTION OF THE DRAWINGS

The features, aspects, and advantages of the invention will become more thoroughly apparent from the following detailed description, appended claims, and accompanying drawings in which:

DETAILED DESCRIPTION

Figure 1:
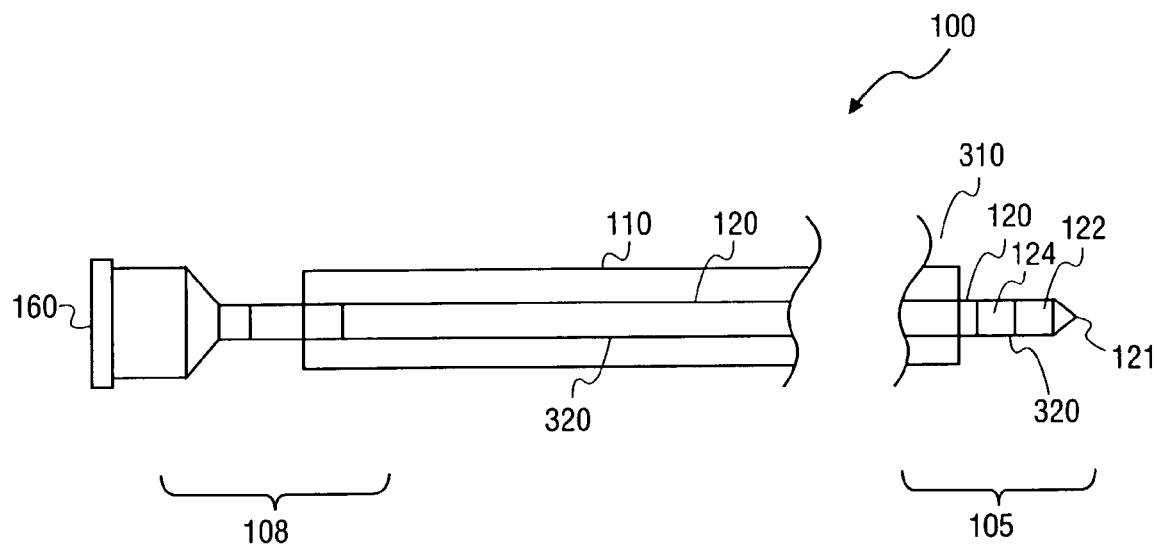
FIG. 1 shows a cross-sectional side view of an embodiment of a substance delivery apparatus including a single delivery device having both a treatment agent and a compound that forms a bioerodable gel in a mammalian host within the delivery apparatus.

In connection with the description of the various embodiments, the following definitions are utilized:

"Therapeutic angiogenesis" refers to the processes of causing or inducing angiogenesis and arteriogenesis.

"Angiogenesis" is the promotion or causation of the formation of new blood vessels in the ischemic region.

"Arteriogenesis" is the enlargement of pre-existing collateral vessels. The collateral vessels allow blood to flow from a well-perfused region of the vessel into the ischemic region.

"Ischemia" is a condition where oxygen demand of the tissue is not met due to localized reduction in blood flow caused by narrowing or occlusion of one or more vessels. Narrowing of arteries such as coronary arteries or their branches, is most often caused by thrombosis or via deposits of fat, connective tissue, calcification of the walls, or restenosis due to abnormal migration and proliferation of smooth muscle cells.

"Occlusion" is the total or partial obstruction of blood flow through a vessel.

"Treatment agent" includes medicaments such as a drug used in the prevention, alleviation, or cure of disease or injury, including, but not limited to, agents directed to specific cellular binding sites (e.g., receptor binding treatment agents) and agents that induce inflammation.

"Specific binding treatment agent" or "receptor binding treatment agent" includes a protein or small molecule that will induce and/or modulate a therapeutic angiogenic response through interaction with a specific binding sites (e.g., a binding within a cell or on a cell surface). Representative treatment agents include, but are not limited to, vascular endothelial growth factor (VEGF) in any of its multiple isoforms, fibroblast growth factors, monocyte chemoattractant protein 1 (MCP-1), transforming growth factor beta (TGF-beta) in any of its multiple isoforms, transforming growth factor alpha (TGF-alpha), lipid factors, hypoxia-inducible factor 1-alpha (HIF-1-alpha), PR39, DEL 1, nicotine, insulin-like growth factors, placental growth factor (PlGF), hepatocyte growth factor (HGF), estrogen, follistatin, proliferin, prostaglandin E1, prostaglandin E2, cytokines, tumor necrosis factor (TNF-alpha), erythropoietin, granulocyte colony-stimulating factor (G-CSF), granulocyte macrophage colony-stimulating factor (GM-CSF), angiogenin, hormones, and genes that encode such substances.

"Non-specific treatment agent" includes various agents that induce inflammation. Examples include bioresorbable inorganic compounds such as sol gel particles and calcium phosphate glass comprising iron; fibrin, gelatin, low molecular weight hyaluronic acid, and chitin; bacterial polysaccharides; and metals.

In the embodiments described herein, a substance delivery device and a method for delivering a substance are disclosed. The delivery device and method described are particularly suitable, but not limited to, local drug delivery in which a treatment agent composition (possibly including multiple treatment agents and/or a sustained-release composition) is introduced via needle delivery to a treatment site within a mammalian host. A kit of a treatment agent composition is also described. One suitable application for a delivery device is that of a catheter device, including a needle delivery system. Suitable therapies include, but are not limited to, delivery of drugs for the treatment of arterial restenosis, therapeutic angiogenesis, or cancer treatment drugs/agents.

Various apparati (devices) and methods described herein can be used as a stand-alone injection needle/catheter during a surgical procedure such as an open heart surgery (e.g., Cabbage Coronary Bypass Graft (CABG)) procedure in which areas of the heart may be treated with, for example, growth factors, for affecting therapeutic angiogenesis, or incorporated into a catheter-based system to access locations that are commonly used in percutaneous translumenal coronary artery (PTCA) procedures. The apparati (devices) and methods may similarly be used in other surgical procedures such as cancer-related procedures (e.g., brain, abdomen, or colon cancer procedures or surgeries). Additionally, various apparati (devices) and methods described herein can be used in conjunction with various catheter-related or endoscopy procedures that generally require minimal invasiveness to deliver a specific drug or growth factor into tissue. Examples of such procedures include, but are not limited to, orthoscopic surgery for joints (e.g., knee), laparoscopic surgery for the abdomen, and thoroscopic procedures related to chest injuries or treatments.

One concern of introducing any treatment agent composition, whether adjacent a blood vessel to affect therapeutic angiogenesis, adjacent a tumor to inhibit tumor growth, or to induce or stimulate collagen growth in orthroscopic procedures, is that the composition remain (at least partially) at the treatment site for a desired treatment duration (or a portion of the treatment duration). In this manner, an accurate dosage may be placed at a treatment site with reduced concern that the treatment agent will disperse, perhaps with serious consequences.

In one embodiment, a composition and technique for retaining a treatment agent at a treatment site (injection site) is described. In one embodiment, a treatment agent and a bioerodable gel are introduced at a treatment site (e.g., an injection site). The bioerodable gel may be introduced prior to, after, or simultaneously with the treatment agent. In one preferred embodiment, the bioerodable gel acts to retain the treatment agent at the treatment site by, representatively, sealing the treatment site or sealing the treatment agent at the treatment site. The use of a bioerodable gel with a treatment agent can reduce the amount of treatment agent backflow from the injection site as well as reduce the load requirement of the treatment agent at the treatment site. For example, a bioerodable gel can decrease the local pressure thereby further resulting in backflow reduction.

In the area of cardiovascular treatment therapies, the treatment agent may be a treatment agent that affects (e.g., induces and/or modulates) therapeutic angiogenesis. Suitable therapeutic angiogenesis treatment agents include, but are not limited to, one or more of a specific binding treatment agent. The treatment agent may further include or be included in a sustained-release matrix that delays the release of the treatment agent over a period of time (such as over several hours to several days). Suitable sustained-release matrix material for therapeutic angiogenesis treatment agents include, but are not limited to, poly(L-lactide), poly(D,L-lactide), poly(glycolide), and poly(lactide-co-glycolide) (PLGA) compositions. Another suitable treatment agent is a non-specific treatment agent such as one that may induce inflammation. Reducing the backflow on introduction of the treatment agent through the use of a gel may inhibit possible thrombogenic effects of a treatment agent that induces inflammation. Although cardiovascular treatment agents are described, it is appreciated that other treatment agents are also contemplated, with one limit being those treatment agents that are compatible with a bioerodable gel material.

In one embodiment, particularly in the case of cardiovascular treatment therapies, the bioerodable gel material is selected to have a property that is non-thrombogenic. Suitable materials include material such as polyphosphoester gels, such as a polyphosphoester with a low glass transition temperature (e.g., POLIHEXOFATE™ polymer, commercially available from Guilford Pharmaceuticals of Baltimore, Md. (a copolymer of 1,4-cyclohexanedimethanol and n-hexylphosphate). Another suitable bioerodable gel is a gel formed from a moderately high glass transition temperature by a resolvable polymer that is plasticized in a pharmaceutical water solvent, such as glucofurol to form the gel. In this latter case, the solvent is selected to be rapidly absorbed by the body leaving the bioerodable material at the injection site. Other polymer materials include poly(glycolic lactic) acid (PLGA), caprolactone, and cyanoacrylate polymers. A third bioerodable gel material is one that is formed by a combination (e.g., mixing, contacting, reacting) of two or more components. One example is a an alginate (alginic acid) and calcium chloride that combine to form a gel on contact within a mammalian host.

Accordingly, in one embodiment, a technique is described for introducing a treatment agent at a location in a mammalian host. Specifically, the technique comprises utilizing a delivery device for introducing a treatment agent and a compound that forms a bioerodable gel at a treatment site so as to increase the retention of the treatment agent at the treatment site.

Referring now to the drawings, wherein similar parts are identified by like reference numerals, FIG. 1 illustrates a cross-sectional side view of one embodiment of a delivery device or apparatus. In general, delivery assembly 100 provides an apparatus for delivering a substance, such as a treatment agent or a combination of treatment agents and a composition that forms a bioerodable gel in a mammalian host, to or through a desired area of a blood vessel (a physiological lumen) or tissue in order to treat a localized area of the blood vessel or to treat a localized area of tissue, possibly located adjacent to the blood vessel. Delivery assembly 100 is intended to broadly include any medical device designed for insertion into a blood vessel or physiological lumen to permit introduction (e.g., injection) of a treatment agent.

Referring to FIG. 1, delivery assembly 100, in one embodiment, may be in the form of a catheter delivery device that includes delivery lumen 110 that may be formed in a larger catheter body (not shown). The larger catheter body may include one or more lumens to accommodate, for example, a guidewire, an inflation balloon, and/or an imaging device. Further, such a catheter body may accommodate one or more delivery lumens, such as delivery lumen 110. Delivery lumen 110, in this example, extends between distal portion 105 and proximal portion 108 of delivery assembly 100. Delivery lumen 110 can be made from any suitable material, such as polymers and co-polymers of polyamides, polyolefins, polyurethanes, and the like.

In one embodiment, delivery assembly 100 includes needle 120 movably disposed within delivery lumen 110. Needle 120 is, for example, a stainless steel hypotube that extends a length of the delivery assembly. Needle 120 includes a lumen with an inside diameter of, representatively, 0.16 inches (0.40 centimeters). In one example for a retractable needle catheter, needle 120 has a length on the order of 40 inches (1.6 meters) from distal portion 105 to proximal portion 108. At an end of proximal portion 108 is adapter 160 of, for example, a female luer housing.

Referring to distal portion 105 of delivery assembly 100, there is shown needle 120 having treatment agent 122 disposed at or near its tip (tip 121). In one example, treatment agent 122 is a material selected for its ability to affect therapeutic angiogenesis.

Disposed proximally (as viewed) to treatment agent 122 in needle 120 is gel material 124 that has a property such that it will form a bioerodable gel when placed at a treatment site (e.g., in the wall of a blood vessel, in a periadventitial space, in an area radially outward from a periadventitial space, etc.). Suitable materials for gel material include, but are not limited to, the polyphosphoester gels and bioresorbable polymers (possibly dissolved in a solvent), such as PLGA, caprolactone or cyanoacrylate polymers referenced above.

One technique to load treatment agent 122 and gel material 124 into a catheter delivery device is by creating an area (volume) of reduced pressure in needle 120 by, for example, a syringe bore. First, distal portion 105 is placed in a solution having a selected concentration of gel material 124, such as on the order of about 11 microliters (approximately 3-4 milligrams of polymer or 25 weight percent). Through a pressure differential, a desired amount of gel material 124 is taken up by needle 120.

Following the loading of gel material 124, needle 120 (distal portion 105 of needle 120) is placed in a solution comprising a selected concentration of treatment agent 122 which, as is appreciated, will vary with the particular treatment and/or treatment agent. Again by a reduced pressure in needle 120, a desired amount of a treatment agent is taken up by needle 120.

In certain instances, it may be desired to combine the treatment agent and the gel material into a single composition and introduce the single composition to a treatment site. Such an instance may be one where the combination (e.g., mixing) of the gel material and the treatment agent does not inhibit (or minimally inhibits) the properties of the treatment agent. One example in the context of cardiovascular treatment therapies is a treatment agent that affects therapeutic angiogenesis by inducing inflammation, such as a metal (e.g., Au). It is appreciated in such instances that a solution composition of a gel material and a treatment agent may be loaded into needle 120 by a pressure differential as described or may be introduced through adaptor 160 (such as through a needle luer).

Once loaded, such as described above, treatment agent 122 and gel material 124 may be introduced according to known substance delivery techniques such as by advancing tip 121 of needle 120 into tissue (e.g., a wall of a blood vessel) and delivering the treatment agent and gel material through back pressure (e.g., pressure applied at proximal portion 108, such as by a needle luer). Needle 120 may form a wound (wound opening) in tissue at the treatment site. The introduction of gel material 124 following treatment agent 122 will tend to contain (retain) treatment agent 122 within the wound opening, thus reducing backflow.

Figure 2:
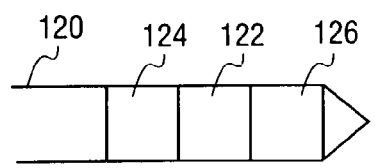
FIG. 2 shows a cross-sectional side view of a second embodiment of a delivery apparatus having both a treatment agent and a compound that may form a bioerodable gel in a mammalian host.

FIG. 2 shows an alternative loading arrangement within needle 120. In this embodiment, treatment agent 122 is disposed between gel material. Again, each of the materials may be loaded in needle 120 through pressure differential techniques. One order is loading gel material 124, followed by treatment agent 122, followed by gel material 126.

The configuration shown in FIG. 2 of treatment agent 122 disposed between gel material 124 and gel material 126 may be used, representatively, in a situation where it is desired to retain the treatment agent within needle 120 until delivery (e.g., to prevent the loss of a portion of treatment agent 122 prior to delivery at a treatment site within a mammalian host).

Figure 3:
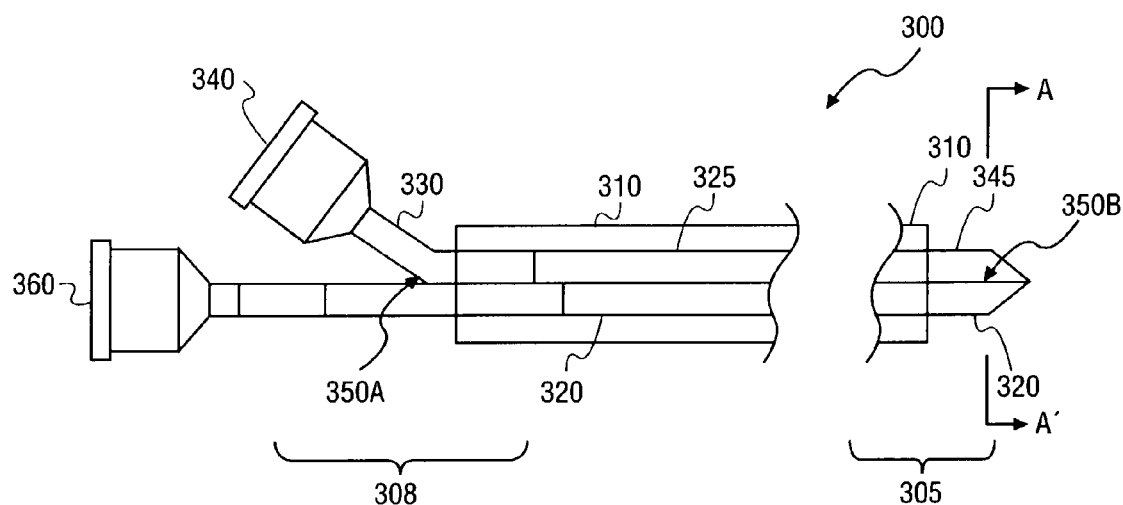
FIG. 3 illustrates a simplified, cross-sectional side view of an embodiment of a substance delivery apparatus in the form of a catheter assembly including linear-aligned delivery lumens for a treatment agent and a compound that forms a bioerodable gel within a mammalian host.

FIG. 1 and FIG. 2 describe embodiments of techniques for introducing a treatment agent and a gel material, such as a bioerodable gel material, to a treatment site within a mammalian host (e.g., human). Such embodiments are particularly suitable for use with gel material that may be introduced in a single composition either as a gel (e.g., dispersed in solvent) or to form a gel within a mammalian host. FIG. 3 presents an embodiment of an apparatus that may be used to introduce a material that is a combination of two materials that, when combined in a mammalian host, form a bioerodable gel. One example of such a gel material is an alginate and calcium chloride.

FIG. 3 presents delivery assembly 300 of, for example, a catheter-compatible device or apparatus. Delivery assembly 300 includes delivery lumen 310 of, for example, a polymer material that may be formed in a larger catheter body (not shown). The larger catheter body may include one or more other lumens to accommodate, for example, an additional delivery device lumen, a guidewire an inflation balloon, and/or imaging device. Delivery lumen 310, in this example, extends between distal portion 305 and proximal end 308 of delivery assembly 300.

Figure 4:
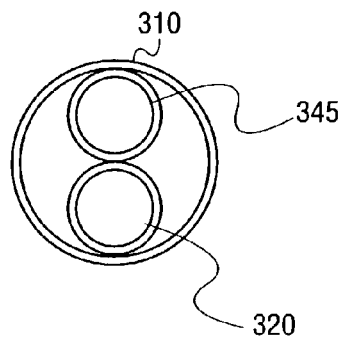
FIG. 4 shows a cross-sectional front view of a distal end of the delivery apparatus of FIG. 3.

In one embodiment, delivery assembly 300 includes main needle 320 disposed within delivery lumen 330. Main needle 320 is movably disposed within delivery lumen 330. Main needle 320 is, for example, a stainless steel hypotube that extends a length of the delivery assembly. Main needle 320 includes a lumen with an inside diameter of, for example, 0.08 inches (0.20 centimeters). In one example for a retractable needle catheter, main needle 320 has a needle length on the order of 40 inches (1.6 meters) from distal portion 305 to proximal portion 308. Delivery lumen 310 also includes separate, possibly smaller diameter, auxiliary lumen 325 extending, in this example, co-linearly along the length of the catheter (from a distal portion 305 to proximal portion 308). Auxiliary lumen 325 is, for example, a polymer tubing of a suitable material (e.g., polyamides, polyolefins, polyurethanes, etc.). At distal portion 305, auxiliary lumen 325 is terminated to auxiliary needle end 345 co-linearly aligned with a delivery end of needle 320. Auxiliary lumen 325 may be terminated to auxiliary needle end 345 with a radiation-curable adhesive, such as an ultraviolet curable adhesive. Auxiliary needle end 345 is, for example, a stainless steel hypotube that is joined co-linearly to the end of main needle 320 by, for example, solder (illustrated as joint 350B). Auxiliary needle end 345 has a length on the order of about 0.08 inches (0.20 centimeters). FIG. 4 shows a cross-sectional front view through line A-A' of delivery assembly 300. FIG. 4 shows main needle 320 and auxiliary needle 345 in a co-linear alignment.

Referring to FIG. 3, at proximal portion 308, auxiliary lumen 325 is terminated to auxiliary side arm 330. Auxiliary side arm 330 includes a portion extending co-linearly with main needle 320. Auxiliary side arm 330 is, for example, a stainless steel hypotube material that may be soldered to main needle 320 (illustrated as joint 350A). Auxiliary side arm 330 has a co-linear length on the order of about, in one example, 1.2 inches (3 centimeters).

The proximal end of main needle 320 includes adaptor 360 for accommodating a substance delivery device (e.g., a substance of a treatment agent or bioerodable gel material). Adaptor 360 is, for example, a molded female luer housing. Similarly, a proximal end of auxiliary side arm 330 includes adaptor 340 to accommodate a substance delivery device (e.g., a female luer housing).

The design configuration described above with respect to FIG. 3 is suitable for introducing a bioerodable gel into two parts form. For example, a gel formed by a combination (mixing, contact, etc.) of an alginate and calcium chloride. Representatively, a 3.5 percent of an alginate solution may be introduced by a one cubic centimeters syringe at adaptor 360 through main needle 320. At the same time or shortly before or after, a solution of calcium chloride may be introduced with a one cubic centimeter syringe at adaptor 340. When the alginate and calcium chloride combine at the exit of delivery assembly 300 (at a treatment site), the materials combine (mix, contact) to form a bioerodable gel. One example of a suitable amount of two material gel components for use in a cardiovascular treatment therapy is approximately 200 microliters of alginate solution and one milliliter calcium chloride. Excess calcium chloride may flush through the host as a saline solution. In one embodiment, a desired amount of a treatment agent may be introduced with the alginate solution.

Figure 5:
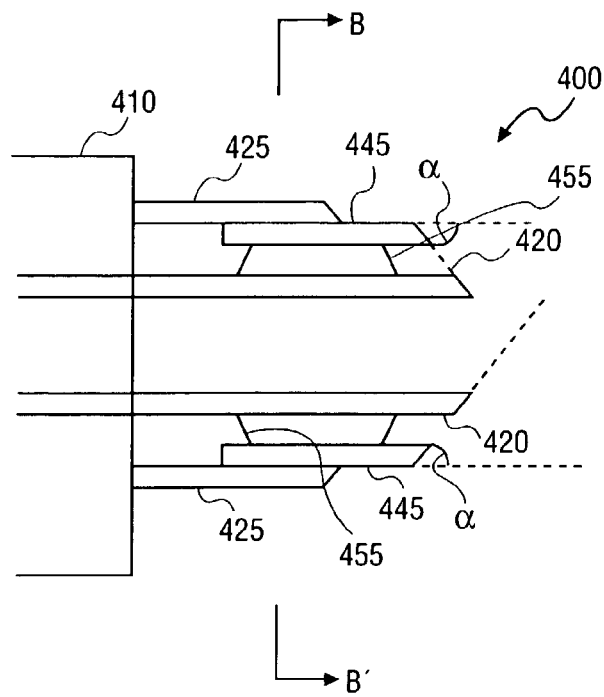
FIG. 5 shows a cross-sectional side view of a distal portion of a second embodiment of a substance delivery apparatus having a co-axial configuration for the delivery of the treatment agent and a compound that forms a gel within a mammalian host.

FIG. 5 shows a second embodiment of a delivery assembly for delivering a two part composition to a treatment site through a needle. In one embodiment, the two part composition may be components that collectively form a bioerodable gel once inside a mammalian host.

FIG. 5 illustrates a co-axial alignment for delivering a two part composition to a treatment site. In this example, delivery assembly 400 includes delivery lumen 410 to accommodate any co-axial needle configuration. Delivery lumen 410 extends, for example, the length of the catheter assembly, from a distal portion to a proximal portion. In the embodiment illustrated in FIG. 5, only the distal portion of delivery assembly 400 is illustrated. The proximal portion may be similar to that described above with respect to FIG. 3 (e.g., separate ports for introducing separate compositions into a single delivery lumen).

Referring to FIG. 5, delivery assembly 400 includes main needle portion 420 of, for example, a stainless steel hypotube material having a lumen diameter on the order of 0.08 inches (0.20 centimeters) and extending the length of the delivery assembly (from distal portion to proximal portion). Surrounding main needle portion 420, in this example, is auxiliary needle portion 445. Auxiliary needle portion 445 has a larger diameter than the diameter of main needle portion 220 such that an opening or a lumen is created between main needle portion 420 and auxiliary portion 445 to allow the introduction of a material therethrough. An exemplary interior diameter of auxiliary needle portion 445 is on the order of 0.16 inches (0.40 centimeters).

Auxiliary needle portion 445 is, for example, stainless steel hypotube material that may be coupled to main needle portion 420 through support vanes 455 (e.g., by laser welding support vanes to auxiliary needle portion 445 and main needle portion 420). Auxiliary needle portion 445 may extends the entire length of needle assembly 400 (i.e., from distal portion to proximal portion) or may comprise only a tip or end portion of, for example, 0.02 to 0.08 inches (0.05 to 0.2 centimeters). In the latter case, auxiliary lumen 425 of, for example, a polymer material may extend through delivery assembly 400 and be terminated to auxiliary needle portion 445 with, for example, a radiation-curable adhesive.

FIG. 5 shows main needle portion 420 having an end (a distal end) portion extending beyond auxiliary needle portion 445. In this manner, the distal end of delivery assembly 420 may be configured as an angle tip, with an angle α, of between, for example, 15 degrees to 45 degrees to allow the penetration of tissue with the end of delivery device 400. The angle α extends around the assembly.

Figure 6:
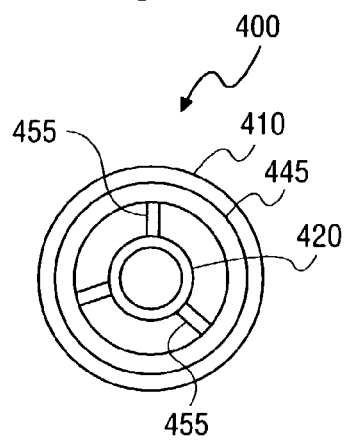
FIG. 6 shows a cross-sectional front view of a distal end of the delivery apparatus of FIG. 5.

FIG. 6 shows a cross-sectional front view of delivery assembly 400 through line B-B' of FIG. 5. FIG. 6 shows main needle portion 420 co-axially surrounded by auxiliary needle portion 445 with support vanes 455 extending between main needle portion 420 and auxiliary needle portion 445.

In an embodiment where a two part composition of an alginate and calcium chloride is introduced to form a bio-erodable gel, the low viscosity medium (calcium chloride) may be introduced (injected) through the outer annular portion (defined by the lumen between main needle portion 420 and auxiliary needle portion 445). The higher viscosity medium calcium chloride may be introduced through the lumen defined by main needle portion 420.

Figure 7:
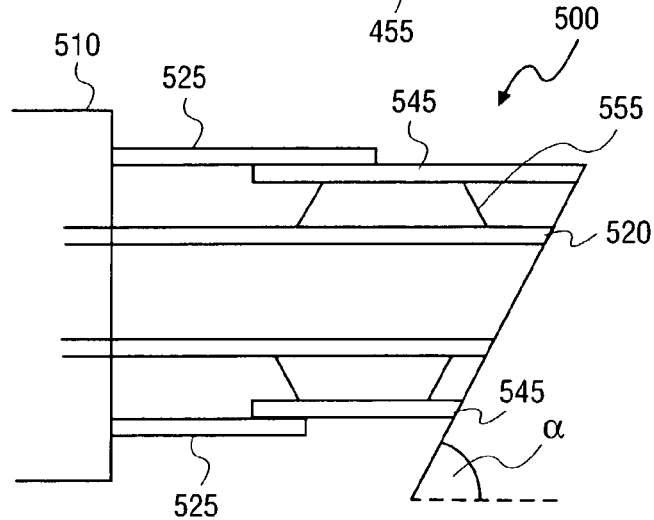
FIG. 7 shows a cross-sectional side view of a distal portion of a second embodiment of a substance delivery apparatus having a co-axial configuration for the delivery of the treatment agent and a compound that forms a gel within a mammalian host.

FIG. 7 shows a cross-sectional side view of a third embodiment of a delivery device for delivering a multi-component material to a treatment site. The configuration shown in FIG. 7 is also a co-axial arrangement (similar to FIGS. 5 and 6). Delivery assembly 500 includes delivery lumen 510, main needle portion 520, auxiliary portion 545, co-axially surrounding main needle portion 520. In this embodiment, main needle portion 520 extends, representatively, the length of delivery assembly 500 (from distal portion to proximal portion). Auxiliary needle portion 545 is a tip portion of, for example, a stainless steel hypotube material that may be coupled to main needle portion 520 by support vanes 555. Auxiliary lumen 525 of, for example, a polymer material may extend the length of delivery assembly 500 and be terminated at auxiliary needle portion 545 with an adhesive (e.g., a radiation-curable adhesive).

In the embodiment shown in FIG. 7, the distal end of delivery assembly 500 includes an angle tip formed by main needle portion 520 and auxiliary needle portion 545. From this example, the tip is a single angle tip, with an end angle, α, on the order of 15 degrees to 45 degrees. In this manner, the angle tip allows for insertion into tissue.

Figure 8:
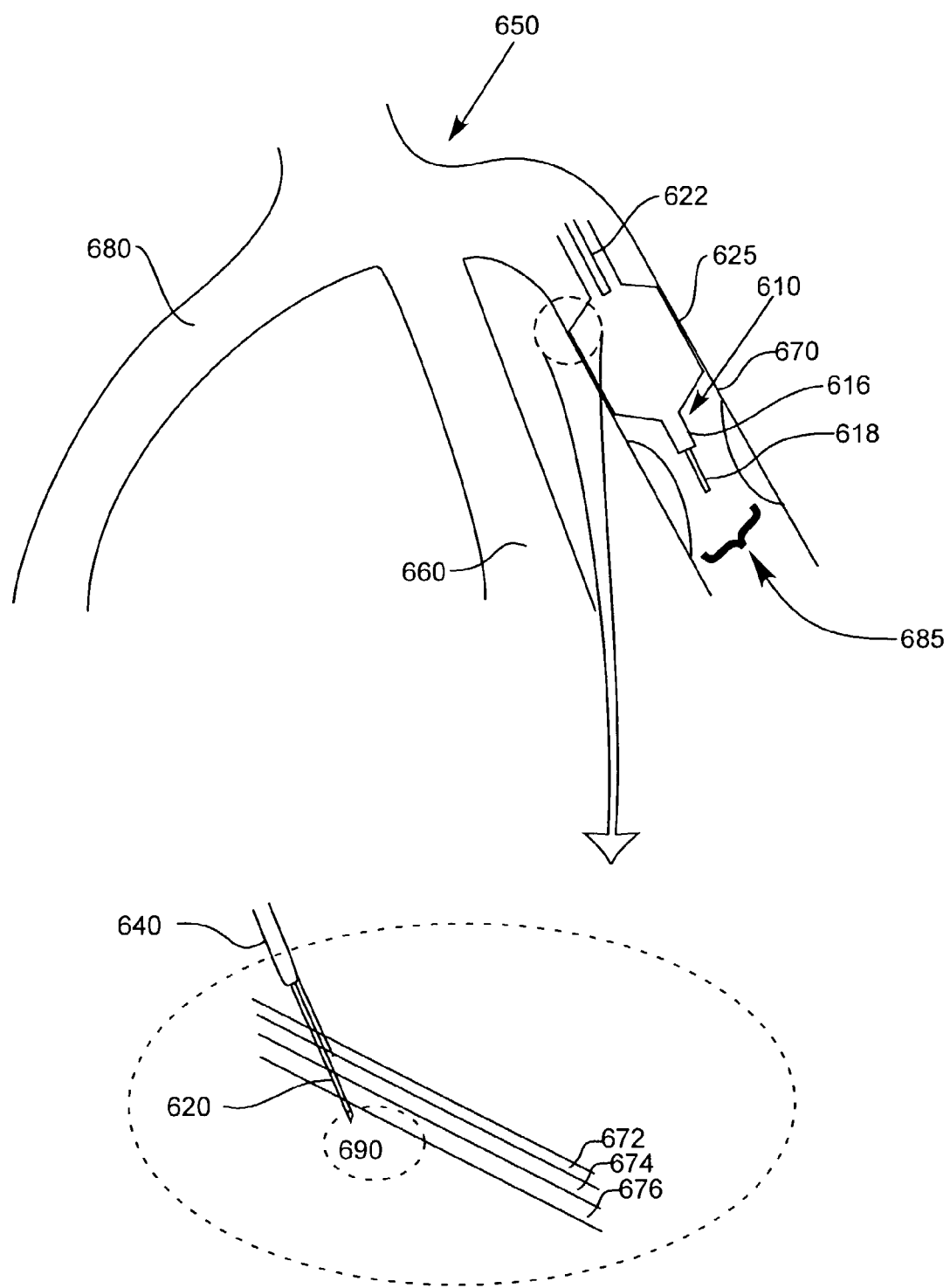
FIG. 8 schematically illustrates a coronary artery network with a catheter assembly introduced therein.

The catheter assemblies described with reference to FIGS. 1-7 may be used to introduce a treatment agent and a gel such as described above at a desired location. FIG. 8 illustrates one technique.

FIG. 8 illustrates components of a coronary artery network. In this simplified example, vascular 650 includes left anterior descending artery (LAD) 660, left circumflex artery (LCX) 670 and right coronary artery (RCA) 680. Occlusion 685 is shown in LCX 670. Occlusion 685 may limit the amount of oxygenated blood flow through LCX 670 resulting in ischemia in the tissues distal (downstream) to the occlusion. To improve the function of the artery network, it is generally desired to either remove occlusion 685 (for example, through an angioplasty procedure), bypass occlusion 685 or induce therapeutic angiogenesis to make-up for the constriction in the ischemic region.

With reference to FIG. 8, in a one procedure, guidewire 618 is introduced into, for example, the arterial system of the patient (e.g., through the femoral artery) until the distal end of guidewire 618 is upstream of a narrowed lumen of the blood vessel (e.g., upstream of occlusion 685). Delivery assembly 600 (in this example, a balloon catheter device) is mounted on the proximal end of guidewire 618 and advanced over guidewire 618 via lumen 616 until positioned as desired. In the example shown in FIG. 8, delivery assembly 600 is positioned so that catheter balloon 625 and a delivery lumen 640 (see, e.g., delivery lumen 110 (FIG. 1); delivery lumen 310 (FIG. 3); delivery lumen 410 (FIG. 5); delivery lumen 510 (FIG. 7)) are upstream of the narrowed lumen of LCX 670. Angiographic or fluoroscopic techniques may be used to place delivery assembly 600. Once catheter balloon 625 is placed, a treatment site of the blood vessel may be identified by further imaging techniques, including but not limited to, optical coherence tomography, ultrasonic, or magnetic resonance techniques. An example of an optical imaging technique is described in co-pending commonly-assigned U.S. patent application Ser. No. 10/011,071 where catheter balloon 630 is subject to low inflation pressure and guidewire 618 is removed and replaced in one embodiment with an optical fiber. In the catheter assembly shown in FIG. 8, the imaging portion of an imaging device (e.g., OCT, ultrasonic, etc.) may be within the imaging lumen as the catheter is positioned. Once positioned, in this case upstream of occlusion 685, the imaging assembly is utilized to view the blood vessel and identify the various layers of the blood vessel.

The imaging assembly may provide viewable information about the thickness or boundary of the intimal layer 672, media layer 674, and adventitial layer 676 of LCX 670. LCX 670 is viewed and the layer boundary is identified or a thickness of a portion of the blood vessel wall is imaged (and possibly measured). The treatment site may be identified based on the imaging (and possibly measuring). In one example, the treatment site is a peri-adventitial site (e.g., site 678) adjacent to LCX 670.

After identifying a treatment site, catheter balloon 625 is dilated as shown in FIG. 8 by, for example, delivering a liquid or gas to catheter balloon 625 through inflation lumen 622. Delivery lumen 640, in this example, is coupled to a proximate tapered wall of catheter balloon 620 such that, as catheter balloon 620 is inflated, delivery lumen 640 moves proximate to or contacts the blood vessel wall adjacent to the treatment site. The delivery assembly (device) described is similar in certain respects to the assembly (device) described in commonly-owned U.S. patent application Ser. No. 09/746,498 (filed Dec. 21, 2000) titled "Directional Needle Injection Drug Delivery Device," of Chow, et al., that is incorporated herein by reference. Needle 630 is then advanced a distance into the wall of the blood vessel. A real time image may be used to advance needle 620. Alternatively, the advancement may be based on a measurement of the blood vessel wall or layer boundary derived from an optical image. Needle 620 may be, for example, similar to designs described above with reference to FIGS. 1 and 2 (needle 120). Alternatively, needle 620 may be a dual needle assembly similar to delivery assembly 300 described with reference to FIGS. 3 and 4 (e.g., main needle 320 and auxiliary lumen 325/auxiliary needle 345). As a further alternative, needle 620 may be similar to the embodiment described with reference to FIGS. 5 and 6 (main needle portion 420 and auxiliary needle portion 445) or FIG. 7 (main needle portion 520 and auxiliary needle portion 545).

In the embodiment shown in FIG. 8, needle 620 is advanced through the wall of LCX 670 to peri-adventitial site 690. Once in position, a treatment agent and gel are introduced through needle 620 to the treatment site (e.g., peri-adventitial site 690).

In the preceding detailed description, specific embodiments are presented. Those embodiments include apparati (devices) and methods for introducing a treatment agent and a gel at a treatment site within a mammalian body. Cardiovascular treatment therapies in particular are highlighted. It will, however, be evident that various modifications and changes may be made thereto without departing from the broader spirit and scope of the claims. For example, contemplated treatment therapies include therapies, in addition to cardiovascular treatment therapies, where blood vessels or tissues are identified for localized treatment agents in the context of surgery or other medical procedure. The specification and drawings are, accordingly, to be regarded in an illustrative rather than a restrictive sense.

What is claimed is:

1. A method comprising:
   introducing a first material comprising a treatment agent at a treatment site within a mammalian host; and
   introducing a second material, the second material comprising a property of a bioerodable gel at the treatment site,
   wherein the treatment site comprises a periadventitial site or a site radially outward of a periadventitial site and the treatment site is accessed through a blood vessel.

2. The method of claim 1, wherein the first material and the second material are introduced separately as a combination.

3. The method of claim 1, wherein the second material is a product of a combination of a first component and a second component and one of the first component and the second component comprises the first material.

4. The method of claim 3, wherein introducing the second material comprises:
   introducing a delivery device having a first delivery port and a second separate delivery port, the first delivery port and the second delivery port arranged in one of a co-linear and a co-axial arrangement; and
   introducing the first component to the treatment site through the first delivery port; and
   introducing the second component to the treatment site through the second delivery port.

5. The method of claim 1, wherein introducing the first material comprises:
   advancing a delivery device a distance into a wall of the blood vessel to the treatment site; and
   after advancing the delivery device, introducing the first material through the delivery device.

6. The method of claim 1, wherein the treatment site is a periadventitial site.

7. The method of claim 1, wherein introducing the second material follows the introduction of the first material.

8. The method of claim 1, wherein introducing the second material precedes the introduction of the first material.

9. The method of claim 4, wherein the treatment site is selected from the group consisting of a thoroscopic surgery site, an orthoscopic surgery site, and a laparoscopic surgery site.

10. A method comprising:
    positioning a delivery device at a location in a blood vessel;
    advancing the delivery device a distance into a wall of the blood vessel to a treatment site; and
    after advancing the delivery device, introducing a first material comprising a treatment agent and a second material comprising a property of a bioerodable gel at the treatment site.

11. The method of claim 10, wherein the first material and the second material are introduced as a combination.

12. The method of claim 11, wherein the second material is a product of a combination of a first component and a second component and one of the first component and the second component comprises the first material.

13. The method of claim 12, wherein introducing the second material comprises:
    introducing a delivery device having a first delivery port and a second separate delivery port, the first delivery port and the second delivery port arranged in one of a co-linear and a co-axial arrangement; and introducing the first component to the treatment site through the first delivery port; and introducing the second component to the treatment site through the second delivery port.

14. The method of claim 13, wherein the treatment site is associated with a blood vessel.

15. The method of claim 14, wherein introducing the first material comprises:
    advancing the delivery device a distance into a wall of the blood vessel to the treatment site; and
    after advancing the delivery device, introducing the first material through the delivery device.

16. The method of claim 15, wherein the treatment site comprises a location, with reference to a lumen of the blood vessel, beyond the medial layer of the blood vessel.

17. The method of claim 16, wherein the treatment site comprises a periadventitial site.

18. The method of claim 10, wherein introducing the second material follows the introduction of the first material.

19. The method of claim 10, wherein introducing the second material precedes the introduction of the first material.

* * * * *